United States Patent [19]

Inventi et al.

[11] Patent Number: 5,695,966
[45] Date of Patent: Dec. 9, 1997

[54] DNA ENCODING DAUNORUBICIN 14-HYROXYLASE AND METHOD FOR PREPARING DOXORUBICIN

[75] Inventors: Augusto Solari Inventi, Milan; Umberto Breme, Vigevano; Anna Luisa Colombo, Milan, all of Italy; Charles Richard Hutchinson, Cross Plains; Sharee Otten, Madison, both of Wis.; Claudio Scotti, Motta Visconti, Italy

[73] Assignee: Pharmacia & Upjohn S.p.A., Milan, Italy

[21] Appl. No.: 396,218

[22] Filed: Feb. 27, 1995

[51] Int. Cl.$^6$ .......................... C12P 19/56; C12P 21/04; C12P 21/06; C07H 17/00
[52] U.S. Cl. .......................... 435/78; 435/69.1; 435/71.7; 435/240.1; 536/23.2
[58] Field of Search .......................... 536/23.1; 435/69.1, 435/320.2, 183, 243

[56] References Cited

PUBLICATIONS

Columbo et al. 1992 J Bacteriol 174(5): 1641–1646.
Otten et al 1995 J Bacteriol 177(22):6688–6692.
Otten et al 1990 J Bacteriol 172(6): 3427–3434.

*Primary Examiner*—Robert A. Wax
*Assistant Examiner*—K. Cochrane Carlson
*Attorney, Agent, or Firm*—Nikaido, Marmelstein Murray & Oram, LLP

[57] ABSTRACT

The ability to convert daunorubicin to doxorubicin can be conferred on a host cell by transformation with a recombinant vector comprising DNA encoding daunorubicin 14-hydroxylase. The host cell can then be used to produce doxorubicin.

18 Claims, 3 Drawing Sheets

DNA ENCODING DAUNORUBICIN 14-HYROXYLASE AND METHOD FOR PREPARING DOXORUBICIN

The present invention concerns a process for producing doxorubicin from daunorubicin using an enzyme obtained from a host cell transformed with recombinant DNA.

The anthracyclines of the daunorubicin group, such as doxorubicin, carminomycin and aclacinomycin, are among the most widely employed agents in antitumor therapy [F. Arcamone, Doxorubicin, Academic Press, New York, 1981, pp. 12–25; A. Grein, Process Biochem. 16:34 (1981); T. Kaneko, Chimicaoggi May:11 (1988); C. E. Myers et al., "Biochemical mechanisms of tumor cell kill". In: Anthracycline and Anthracenedione-Based Anti-Cancer Agents (Lown, J. W., ed.), Elsevier, Amsterdam, pp. 527–569, 1988; J. W. Lown, Pharmac. Ther. 60:185–214 (1993)]. Improved derivatives of daunorubicin and doxorubicin have been made by chemical synthesis to enhance their antitumor activity, particularly by the oral route of administration, and to combat the acute toxicity and chronic cardiotoxicity associated with the use of these drugs in the treatment of cancer [Penco, Process Biochem. 15:12 (1980); T. Kaneko, Chimicaoggi May:11 (1988)]. 4'-Epidoxorubicin (Epirubicin), 4-demethoxydaunorubicin (Idarubicin) and methoxy- morpholinodoxorubicin are examples of such analogs.

The anthracyclines are naturally occuring compounds produced by various strains of Streptomyces (*S. peucetius, S. coeruleorubidus, S. galilaeus, S. griseus, S. griseoruber, S. insignis, S. viridochromogenes, S. bifurcus* and Streptomyces sp. strain C5) and by *Actinomyces carminata*. Doxorubicin is mainly produced by *S. peucetius* subsp. caesius while daunorubicin is produced by *S. peucetius* as well as the other Streptomyces described above. The type strains *S. peucetius* subsp. caesius IMRU 3920 (which is the same as ATCC 27952 and is hereinafter abbreviated to "*S. peucetius* 3920"), *S. peucetius* ATCC 29050 ("*S. peucetius* 29050"), *S. peucetius* subsp. caesius ATCC 27952 ("*S. peucetius* 27952") and the daunorubicin non-producing *S. peucetius* dnrN::aphII mutant ("*S. peucetius* dnrN"; S. L. Otten et al., submitted for publication) are publically available. In particular, *S. peucetius* ATCC 27952 is described in U.S. Pat. No. 3,590,028, *S. peucetius* 29050 in U.S. Pat. No. 4,012,284, and *S. peucetius* dnrN has been deposited at the American Type Culture Collection, Rockville, Md. USA, receiving the index number ATCC 55607. *S. peucetius* ATCC 55607 is derived from the *S. peucetius* ATCC 29050 strain by replacing the dnrN gene with a mutant dnrN gene into which the aphII gene from Tn5 (J. M. Ward et al., Mol. Gen. Genet. 203:468–475 (1986)) has been inserted at the SalI site to disrupt the function of dnrN. The *S. peucetius* ATCC 55607 strain is resistant to neomycin or kanamycin, as determined by growth on ISP4 medium (Difco Laboratories, Detroit, Mich.) containing 50 µg/ml of kanamycin, and does not produce doxorubicin, daunorubicin or any of the intermediates of their biosynthesis (S. L. Otten et al., submitted for publication).

The anthracycline doxorubicin is made by *S. peucetius* 27952 from malonic acid, propionic acid, and glucose by the pathway summarized in Grein, Advan. Appl. Microbiol. 32:203 (1987) and in Eckardt and Wagner, J. Basic Microbiol. 28:137 (1988). ε-Rhodomycinone, carminomycin and daunorubicin are established intermediates in this process. The final step in this pathway involves the hydroxylation of daunorubicin to doxorubicin, which is reported to occur only in *S. peucetius* 27952 [F. Arcamone et al., Biotechnol. Bioeng. 11:1101 (1969)]. In EP-A-61737 there is describd a method for the bioconversion of daunorubicin to doxorubicin in about 30% yield, using a daunorubicin non-producing mutant of *S. peucetius* ATCC 31847 obtained from treatment of the strain ATCC 27952 with N-methyl-N'-nitro-N-nitrosoguanidine. However, this conversion usually is done chemically on an industrial scale, according to U.S. Pat. No. 3,803,124.

Genes for daunorubicin biosynthesis and daunorubicin resistance have been obtained from *S. peucetius* 29050 and *S. peucetius* 27952 by cloning experiments [Stutzman-Engwall and Hutchinson, Proc. Natl. Acad. Sci. USA 86:3135 (1989); Otten et al., J. Bacteriol. 172:3427 (1990)]. These studies have shown that, when introduced into *Streptomyces lividans* 1326, the cloned genes confer the ability to produce ε-rhodomycinone and to become resistant to daunorubicin and doxorubicin to this host.

The present invention provides an isolated DNA molecule encoding a daunorubicin 14-hydroxylase. Daunorubicin 14-hydroxylase converts daunorubicin to doxorubicin. The DNA molecule typically consists essentially of the sequence of SEQ ID No: 1, which sequence will be referred to as the "dxrA" sequence. The deduced amino acid sequence of the daunorubicin 14-hydroxylase encoded by SEQ ID No: 1 is shown in SEQ ID No: 2.

The DNA molecule of the invention may comprise all or part of the 3.4 kb SphI fragment of FIG. 1. The sequence encoding daunorubicin 14-hydroxylase is between the KpnI and BamHI sites of the SphI fragment. The DNA molecule of the invention may also comprise all or part of the NdeI—BamHI fragment of FIG. 2. The NdeI—BamHI fragment of FIG. 2 was derived from the slightly larger KpnI—BamHI fragment of FIG. 1.

When the DNA molecule of the invention comprises only part of the 3.4 kb SphI fragment or of the Nde—BamHI fragment, the part must function as a daunorubicin 14-hydroxylase (i.e. it must convert daunorubicin to doxorubicin). The part is typically at least 1.2 kb in length, preferably from 1.2 to 3.4 kb in length, more preferably from 1.2 to 2.4 kb in length. The part may be a restriction enzyme fragment such as the KpnI—BamHI fragment of FIG. 1.

The invention includes a DNA molecule which encodes a daunorubicin 14-hydroxylase having a sequence at least 60% identical to the sequence of SEQ ID No: 2. The invention also includes a daunorubicin 14-hydroxylase having an amino acid sequence at least 60% identical to the sequence of SEQ ID No: 2. The sequence may be at least 80%, at least 90%, at least 95%, at least 98% or at least 99% identical to the sequence of SEQ ID No: 2.

The sequence of SEQ ID No: 2 may be modified by substitution, deletion, insertion, extension, functionalisation or chemical modification. A substitution, deletion, insertion or extension may involve one or more amino acids, for example one, two, three, four, five, eight, fifteen or twenty amino acids. In general, the physicochemical nature of SEQ ID No: 2 should be preserved in a modified sequence. The modified sequence should generally be similar in charge, hydrophobicity/hydrophilicity and size. Candidate substitutions are those which lead to an amino acid from one of the following groups being substituted by a different amino acid from the same group:

H, R and K

I, L, V and M

A, G, S and T

D, E, P and N.

DNA molecules encoding the modified sequences may be made using conventional techniques. For example, they may be made using conventional DNA synthesis, site-directed mutagenesis and recombinant DNA techniques. Suitable techniques are described in Sambrook et al (1989) Molecular Cloning: A Laboratory Manual, 2nd Ed., Cold Spring Harbor Laboratory, Cold Spring Harbor, N.Y. Proteins having derivative sequences may be readily tested for daunorubicin 14-hydroxylase activity, for example using the method described in the Examples below.

For the daunorubicin 14-hydroxylase encoded by the DNA molecules of the invention to be expressed, the DNA may carry its own transcriptional control sequence and, in particular, its own promoter which is operably connected to the coding sequence and which is recognised by a host cell RNA polymerase. Alternatively, the DNA may be ligated to a heterologous transcriptional control sequence in the correct fashion or cloned into a vector at a restriction site appropriately located neighboring a transcriptional control sequence in the vector.

A DNA molecule encoding daunorubicin 14-hydroxylase may be a recombinant DNA cloning or expression vector. Any autonomously replicating and/or integrating agent comprising a DNA molecule to which one or more additional DNA segments can be added may be used. Typically, however, the vector is a plasmid. A preferred plasmid is the high copy number plasmid pWHM3 or pIJ702 [Katz et al., J. Gen. Microbiol. 129:2703 (1983)]. Other suitable plasmids are pIJ385 [Mayeri et al., J. Bacteriol. 172:6061 (1990)], pIJ680 [Hopwood et al., Genetic Manipulation of Streptomyces. A Laboratory Manual, John Innes Foundation, Norwich, UK, 1985], pWHM601 [Guilfoile and Hutchinson, Proc. Natl. Acad. Sci. USA 88:8553 (991)] or pSET152 [Bierman et al., Gene 116:43–49 (1992)]. Any suitable technique may be used to insert the DNA into the vector. Insertion can be achieved by ligating the DNA into a linearized vector at an appropriate restriction site. For this, direct combination of sticky or blunt ends, homopolymer tailing, or the use of a linker or adapter molecule may be employed.

The recombinant vector may be used to transform or transfect a suitable host Cell. The host cells may be ones that are daunorubicin- or doxorubicin-sensitive, i.e. cannot grow in the presence of a certain amount of daunorubicin or doxorubicin, or that are daunorubicin- or doxorubicin-resistant. The host may be a microorganism such as a bacterium. Strains of S. peucetius, in particular S. peucetius dnrN and other strains of Streptomyces species that do not or do produce anthracyclines, respectively, may therefore be transformed. Transformants of Streptomyces strains are typically obtained by protoplast transformation. The vectors may be expressed in non-Streptomycetes, like E. coli.

The daunorubicin 14-hydroxylase protein obtained by the transformed host may be employed for bioconverting daunorubicin to doxorubicin. This method would allow the preparation of highly pure doxorubicin starting from a cell extract produced by a fermentation process and containing daunorubicin.

The bioconversion process can be carried out either by using directly the free or immobilized transformed cells or by isolating the daunorubicin 14-hydroxylase protein, which can be used in the free form or immobilized according to known techniques to resins, glass, cellulose or similar substances by ionic or covalent bonds, or grafted to fibers permeable to the substrate or insolubilized by cross-linkage. The daunorubicin 14-hydroxylase protein may also be used in the raw cellular extract. The recombinant vector of the present invention may also be used to transform a suitable host cell which produces daunorubicin, in order to enhance the bioconversion of daunorubicin to doxorubicin. The host cells may be ones that are daunorubicin- or doxorubicin-resistant, i.e. that can grow in the presence of any amount of daunorubicin or doxorubicin. Strains of S. peucetius, in particular S. peucetius 29050 and other strains of Streptomyces species that produce anthracyclines may therefore be transformed. Transformants of Streptomyces strains are typically obtained by protoplast transformation.

The invention includes a process for producing doxorubicin, which process comprises
 (i) culturing a host cell transformed or transfected with a vector of the invention in the presence of daunorubicin under conditions such that the daunorubicin is converted to doxorubicin, and
 (ii) isolating the doxorubicin from the culture.

In this process, the host cell may be cultured at from 20° to 40° C., for example from 30° to 37° C. The duration of culture in the presence of daunorubicin may be from 6 to 96 hours, for example from 12 to 72 hours. The culture is preferably carried out with agitation. The concentration of daunorubicin in the culture may be from 2 to 200 µg/ml, for example from 10 to 100 µg/ml. The daunorubicin may be added to the culture medium at the start of culture or produced by the host cell during culture.

The DNA molecules of the invention may be obtained from the genomic DNA of S. peucetius 29050. This strain has been deposited at the American Type Culture Collection, Rockville, Md., USA under the accession number ATCC 29050. A strain derived from S. peucetius 29050, like S. peucetius 27952, may also be used, which typically is also able to convert daunorubicin to doxorubicin. The DNA molecules may therefore be obtained by:
 (a) preparing a library of the genomic DNA of S. peucetius 29050 or a strain derived therefrom;
 (b) selecting from the library a clone with the ability to convert daunorubicin to doxorubicin; and
 (c) isolating a DNA molecule of the invention from the selected clone.

The library may be prepared in step (a) by partially digesting the genomic DNA of S. peucetius 29050 or a strain derived therefrom; or by screening a library of S. peucetius genomic DNA that has been enriched for, or specifically contains, the cluster of daunorubicin biosynthesis genes. The restriction enzyme MboI is preferably used for genomic DNA, but for the library containing the cluster of daunorubicin biosynthesis genes, the restriction enzymes BamHI or SphI are preferred. The DNA fragments thus obtained can be size fractionated; fragments from 3 to 5 kb in size are preferred for genomic DNA and 13.5 kb BamHI or 3.4 to 4.9 kb SphI for DNA fragments from the library containing the cluster of daunorubicin biosynthesis genes. These fragments are ligated into a linearized vector such as pWHM3, pIJ702 or pKC505 [M. A. Richardson et al., Gene 61:231 (1987)]. Host cells are transformed with the ligation mixture. Typically, the host cells can not produce daunorubicin and can be daunorubicin- and doxorubicin-sensitive; for example, sensitive to 10 microgram or less of daunorubicin or doxorubicin per ml. For example, S. lividans JI1326 protoplasts (Hopwood et al., Genetic Manipulation of Streptomyces. A Laboratory Manual, John Innes Foundation, Norwich, UK, 1985) may be transformed.

In step (b), the transformants thus obtained are screened for the ability to take up daunorubicin, convert it to doxorubicin, and excrete doxorubicin. Clones able to convert daunorubicin to doxorubicin are identified by chromatographic analysis of extracts of a culture medium containing daunorubicin for the presence of doxorubicin. Such clones are isolated and recombinant vectors contained therein are extracted. On digestion of the recombinant vectors with suitable restriction enzymes in step (c), the *S. peucetius* 29050 DNA inserted into each vector may be identified, sized and mapped. In this way, it may be checked that the vector contains a DNA molecule of the invention.

Further, two or more overlapping inserts may be isolated that are wholly or partly embraced within the DNA of the invention. These may be fused together by cleavage at a common restriction site and subsequent ligation to obtain a DNA of the invention, pared in length using appropriate restriction enzymes if necessary. Restriction fragments of an insert DNA that contains a gene coding for the daunorubicin 14-hydroxylase protein may be obtained in step (c) also by cleaving an insert DNA with an appropriate restriction enzyme.

The following Examples illustrate the invention.

Figure 1:
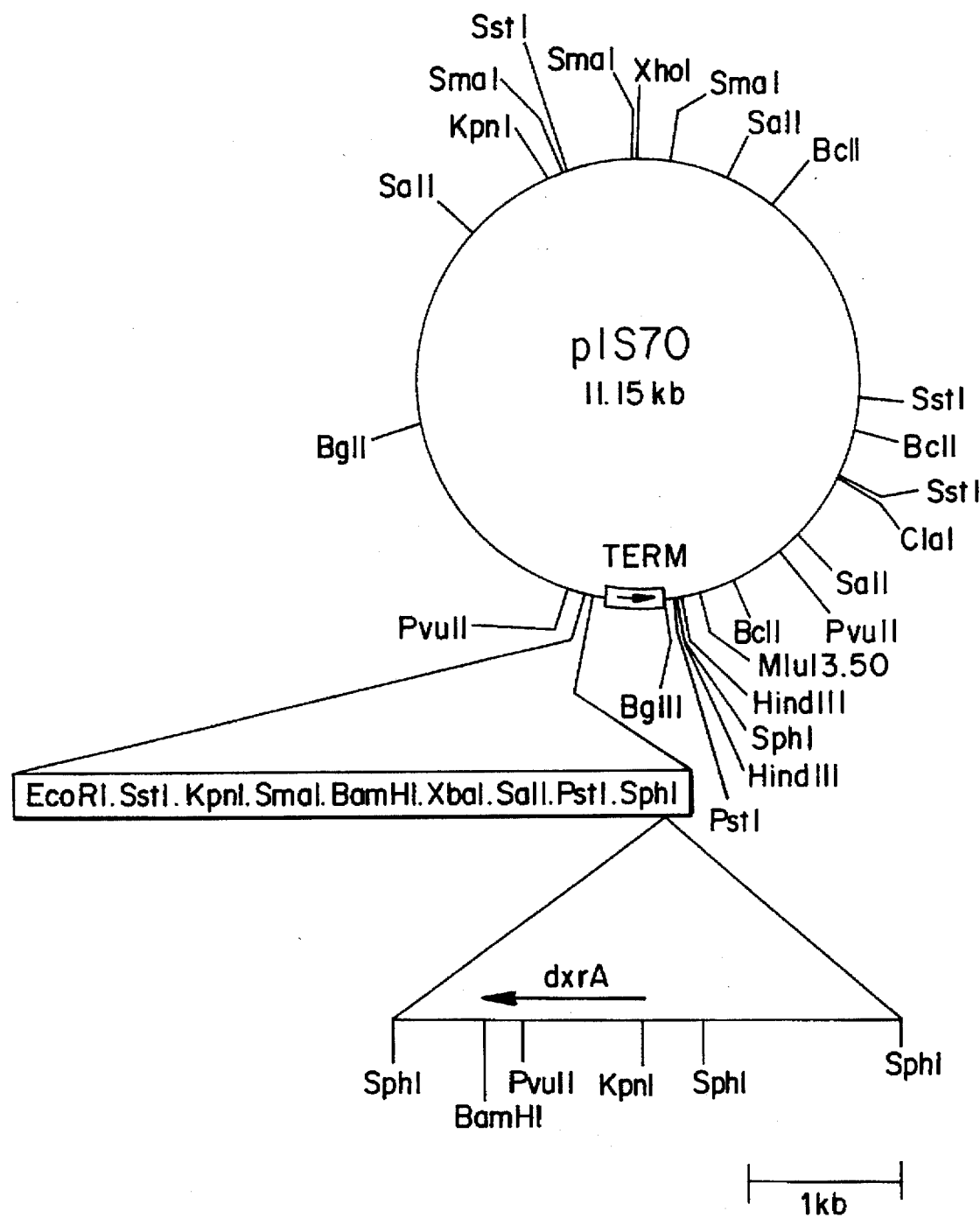
FIG. 1 shows a restriction map of a DNA of the invention. This is an insert in recombinant plasmid pIS70 that was constructed by insertion of a 3.4 kb SphI DNA fragment containing the daunorubicin 14-hydroxylase (dxrA) gene, which was obtained from recombinant plasmid pIS62 by its partial digestion with SphI, into the SphI site of the pWHM3 plasmid, an *Escherichia coli*-Streptomyces shuttle vector [Vara et al., J. Bacteriol. 171:5872 (1989)]. The map shown in FIG. 1 does not necessarily provide an exhaustive listing of all restriction sites present in the DNA segment. However, the reported sites are sufficient for an unambiguous recognition of the segments.

Lane 1, *E. coli* transformed with expression vector pWHM969 (molecular weight of DxrA:42,280); lane 2, *E. coli* transformed with pET-14b (negative control); lane 3, molecular weight standards.

MATERIALS AND METHODS

Bacterial strains and plasmids: *E. coli* strain DH5α, which is sensitive to ampicillin and apramycin, is used for subcloning DNA fragments. *S. lividans* ZX1 [Zhou et al., Nucleic Acids Res. 16:4341 (1988)] and *S. peucetius* dnrN (S. L. Otten et al, submitted for publication) are used for expression of the dxrA gene. The plasmid cloning vectors are pUC18/19 [(Yansch-Perron et al., Gene 33:103 (1985)] and pWHM3 [Vara et al., J. Bacteriol. 171:5872 (1989)].

Media and buffers: *E. coli* DH5α is maintained on LB agar (Sambrook et al., Molecular Cloning. A Laboratory Manual, 2nd ed. Cold Spring Harbor Press, Cold Spring Harbor, N.Y., 1989). When selecting for transformants, ampicillin or apramycin are added at concentrations of 100 μg/ml and 50 μg/ml, respectively. *S. lividans* is maintained on R2YE agar (Hopwood et al., Genetic Manipulation of Streptomyces. A Laboratory Manual, John Innes Foundation, Norwich, UK, 1985) for the preparation of spores as well as for the regeneration of protoplasts.

Subcloning DNA fragments: DNA samples are digested with appropriate restriction enzymes and separated on agarose gels by standard methods (Sambrook et al., Molecular Cloning. A Laboratory Manual, 2nd ed. Cold Spring Harbor Press, Cold Spring Harbor, N.Y., 1989). Agarose slices containing DNA fragments of interest are excised from a gel and the DNA is isolated from these slices using the GENECLEAN device (Bio101, La Jolla, Calif.) or an equivalent. The isolated DNA fragments are subcloned using standard techniques (Sambrook et al., Molecular Cloning. A Laboratory Manual, 2nd ed. Cold Spring Harbor Press, Cold Spring Harbor, N.Y., 1989) into *E. coli* and *E. coli*/Streptomyces shuttle vectors for expression and biotransformation experiments, respectively.

Transformation of Streptomyces species and *E. coli*: Competent cells of *E. coli* are prepared by the calcium chloride method (Sambrook et al., Molecular Cloning. A Laboratory Manual, 2nd ed. Cold Spring Harbor Press, Cold Spring Harbor, N.Y., 1989) and transformed by standard techniques (Sambrook et al., Molecular Cloning. A Laboratory Manual, 2nd ed. Cold Spring Harbor Press, Cold Spring Harbor, N.Y., 1989). *S. lividans* ZX1 mycelium is grown in YEME medium (Hopwood et al., Genetic Manipulation of Streptomyces. A Laboratory Manual, John Innes Foundation, Norwich, UK, 1985) and harvested after 48 hr. The mycelial pellet is washed twice with 10.3% sucrose solution and used to prepare protoplasts according to the method outlined in the Hopwood manual (Hopwood et al., Genetic Manipulation of Streptomyces. A Laboratory Manual, John Innes Foundation, Norwich, UK, 1985). The protoplast pellet is suspended in about 300 microlitres of P buffer (Hopwood et al., Genetic Manipulation of Streptomyces. A Laboratory Manual, John Innes Foundation, Norwich, UK, 1985) and a 50 microlitre aliquot of this suspension is used for each transformation. Protoplasts are transformed with plasmid DNA according to the small-scale transformation method of Hopwood et al. (Hopwood et al., Genetic Manipulation of Streptomyces. A Laboratory Manual, John Innes Foundation, Norwich, UK, 1985). After 17 hr of regeneration on R2YE medium at 30° C., the plates are overlayed with 50 microgram/ml of thiostrepton and allowed to grow at 30° C. until sporulated.

Bioconversion of daunorubicin to doxorubicin: *S. lividans* ZX1 and *S. peucetius* dnrN transformants harboring a plasmid of the invention are inoculated into liquid R2YE medium containing 10 microgram/ml of thiostrepton. After 2 days of growth at 30° C., 2.5 ml of this culture is transferred to 25 ml of production medium [McGuire et al., Process Biochem. 14:2-5(1979)] containing 20 microgram/ml of thiostrepton. Cultures are grown in Erlenmeyer flasks on a rotary shaker at 280 rpm at 30° C. for 72 hr, after which daunorubicin (5 milligram/ml in a water solution) is added to 10 ml of the cultures to give a final concentration of 20 microgram/ml. After 24 hr of further incubation on a shaker, the cultures are incubated in a water bath at 55° C. for 60 min after the addition of 25 milligram/ml of oxalic acid to hydrolyze the glycosidic forms of the anthracycline metabolites. The metabolites are extracted from the cultures with 10 ml of acetonitrile:methanol (1:1) at 30° C. for 30 min on a rotary shaker at 280 rpm. The extract is filtered and the filtrate is analyzed by reversed-phase high pressure liquid chromatography (RP-HPLC). RP-HPLC is performed by using a Vydac C18 column (4.6×250 mm; 5 micrometers particle size) at a flow rate of 0.385 ml/min. Mobile phase A is 0.1% trifluoroacetic acid (TFA, from Pierce Chemical Co.) in H2O and mobile phase B is 0.078% TFA in acetonitrile (from J. T. Baker Chemical Co.). Elution is performed with a linear gradient from 20 to 60% phase B in phase A in 33 minutes and monitored with a diode array detector set at 488 nm (bandwidth 12 micrometers). Daunorubicin and doxorubicin (10 microgram/ml in methanol) are used as external standards to quantitate the amount of these metabolites isolated from the cultures.

EXAMPLE 1

Cloning of the DxrA Gene Encoding Daunorubicin 14-hydroxylase.

Several of the cosmid clones described by Stutzman-Engwall and Hutchinson [(Proc. Natl. Acad. Sci. USA 86:3135 (1989)], such as pWHM337 and pWHM338, or similar clones obtained from equivalent strains, representing from approximately 20 up to 90 kb of S. peucetius 29050 genomic DNA, are partially digested with BamHI, the DNAs are combined and religated, and the resulting mixture of plasmids (containing the pKC505 vector or an equivalent vector that is capable of replication in both E. coli and Streptomyces spp.) is used to transform E. coli DH5 to apramycin resistance (or to the resistance appropriate for selection of the vector used). The plasmid DNAs from sixteen apramycin resistance E. coli clones are introduced into S. lividans ZX1, and the transformants are analysed for the bioconversion of daunorubicin to doxorubicin according to the method described in the Materials and Methods section. Plasmid pIS23 is isolated from a transformant that converts up to 3% of added daunorubicin to doxorubicin, and is found to contain a 13.5 kb insert encompassing the region of the restriction map shown in FIG. 1. The insert in pIS23 is used to subclone a 4.9 kb BglII/ClaI DNA segment into BamHI and AccI digested pUC18. A 4.9 kb EcoRI/HindIII segment is obtained from the resulting plasmid and subcloned into EcoRI and HindIII digested pWHM3 to obtain plasmid pIS62. S. lividans ZX1(pIS62) transformants are prepared as described in the Materials and Methods section and these are tested for the ability to bioconvert daunorubicin to doxorubicin. They can convert up to 16% of added daunorubicin to doxorubicin. A 3.4 kb SphI DNA segment is cloned from pIS62 into the SphI site of pWHM3 to give plasmid pIS70 (FIG. 1). S. lividans ZX1(pIS70) transformants were prepared as described in the Materials and Methods section and are tested for the ability to bioconvert daunorubicin to doxorubicin. They can convert up to 22% of added daunorubicin to doxorubicin.

EXAMPLE 2

Conversion of Daunorubicin to Doxorubicin by a Cell Containing the Daunorubicin 14-hydroxylase Gene but Lacking the Products of Other Daunorubicin Genes The pIS62 and pIS70 plasmids are introduced into the S. peucetius dnrN strain by transformation with selection for thiostrepton resistance, according to the methods described in the Materials and Methods section. The resulting S. peucetius dnrN(pIS62) transformants are tested for the ability to bioconvert daunorubicin to doxorubicin. They can convert up to 58% of added daunorubicin to doxorubicin. The resulting S. peuctius dnrN(pIS70) transformants are tested for the ability to bioconvert daunorubicin to doxorubicin. They can convert up to 100% of added daunorubicin to doxorubicin.

EXAMPLE 3

Expression of DxrA in *Escherichia coli*

The expression vector pET-14b (commercially available from Novagen-Madison, Wis.) is based on the T7 promoter-driven system. When the restriction site Nde I is used, pET-14b allows the expression of a cloned protein fused with an His—Tag at the N-terminus.

A 1373 bp Kpn I≦Bam HI fragment from vector pI S70 (FIG. 1) containing the entire dxrA gene was cloned in pUC19 [Yanish-Perron C. et al., (1985) Gene:33, 103–119]. From the resulting plasmid, a SalI—BamHI fragment was removed and ligated to a KpnI—SalI linker made using two oligonucleotides (51-mer Seq. ID No. 3, and 59-mer Seq. ID No.4) synthesized so that the first codon of dxrA was changed to ATG, which created an Nde I site, and the third position of the fourth, sixth and seventh codons were changed to reflect the most frequently used codon in highly expressed E. coli genes, as a means to enhance the expression of dxrA. The resulting NdeI—BamHI fragment was cloned in pET-14b.

Figure 2:
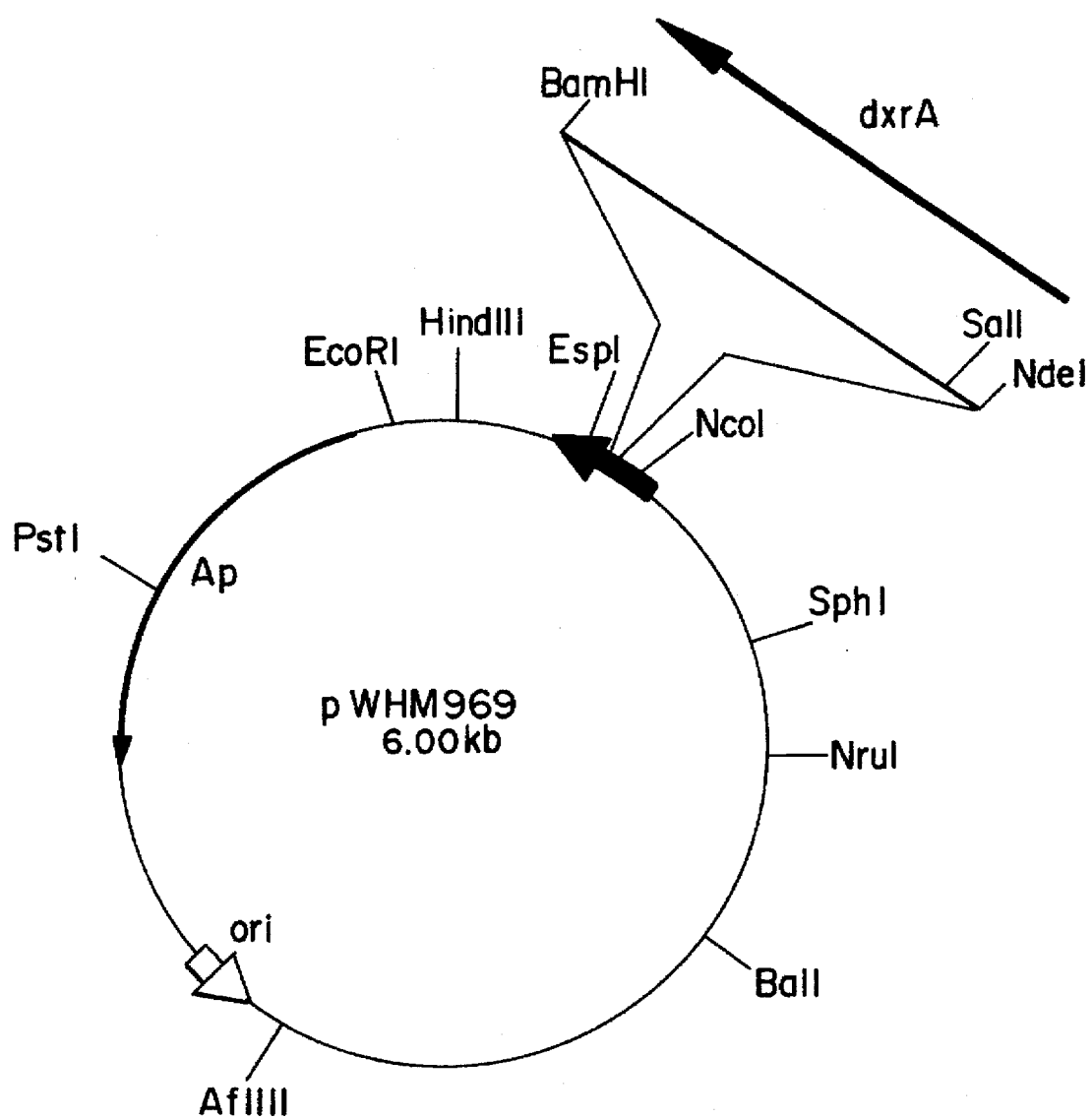
FIG. 2 also shows a restriction map of a DNA of the invention. This is an insert in recombinant plasmid pWHM969 that was constructed by insertion of a 1.33 kb NdeI/BamHI DNA fragment, obtained from the 1.36 kb KpnI/BamHI DNA fragment of pIS70 by site-directed mutagenesis, into the NdeI and BamHI sites of the pET14B *E. coli* expression plasmid vector [Novagen, Madison, Wis.]. In particular, an NdeI restriction site (5'-CAT ATG-3') was inserted in the 1.36 Kb Kpn I/Bam HI DNA fragment by mutagenizing the GTG start codon of the daunorubicin-14-hydroxylase gene as well as the two nucleotides immediately preceeding this start codon so as to reproduce the target sequence recognized by the NdeI restriction enzyme. In order to allow efficient expression of the daunorubicin-14 hydroxylase gene in *E. coli*, the wild type sequence shown in SEQ ID NO.1 was appropriately mutagenized according to the codon usage of *E. coli*. The map shown in FIG. 2 does not necessarily provide an exhaustive listing of all restriction sites present in the DNA segment. However, the reported sites are sufficient for an unambiguous recognition of the segment.

The E. coli host used for expression of the dxrA gene was a λDE3 lysogen of strain BL21 (commercially available from Novagen-Madison Wis.). Expression of dxrA was induced by the addition of IPTG according to the following procedure. 100 ml of 2xYT and ampicillin (50µg/ml) were inoculated with a single colony from a freshly streaked plate of pWHM969 (FIG. 2). Cells were grown at 37° C. until $OD_{600}$=0.4–1.0. Expression of dxrA was induced by adding 4mM IPTG and the incubation was continued for 3–4 hours.

Figure 3:
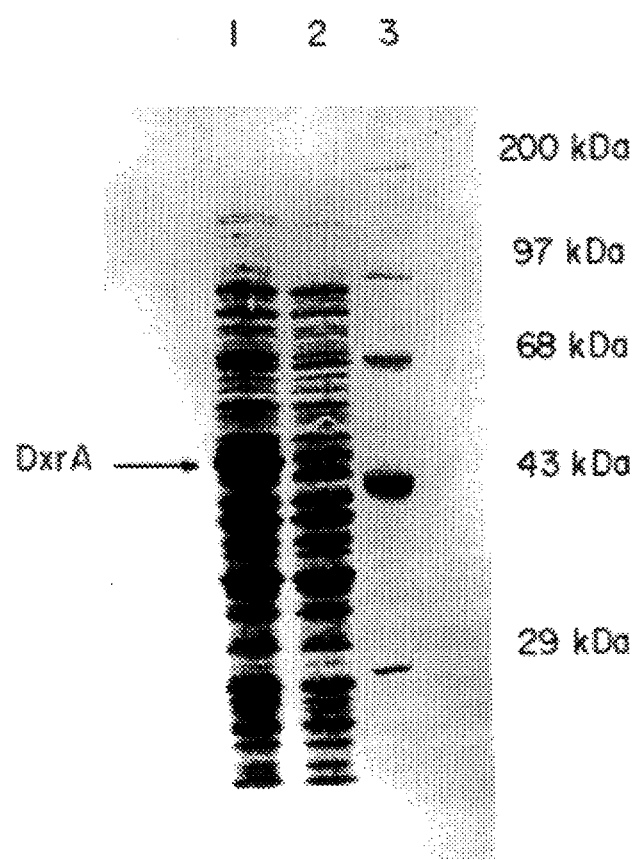
FIG. 3 is a Comassie-stained SDS-polyacrylamide gel of cell extracts from *Escherichia coli* transformed with dxrA expression vectors and induced by IPTG for 4 hours.

0.5 ml of the culture was centrifuged at 14,000 rpm in a microcentrifuge for 1 minute, the supernatant was discarded and the pellet was resuspended in 50 microliters of Laemmli buffer [Laemmli, Nature (London), 227:680 (1970)] and boiled for 5 minutes. The proteins contained in the boiled sample were analyzed on a 10% SDS-polycrilamide gel (FIG. 3) using standard methods [Laemmli, Nature (London), 227:680 (1970)] by comparison with the pET 14b vector that does not contain the dxr A gene.

The daunorubicin 14-hydroxylase preotein migrates at Mr 42,280.

We claim:

1. An isolated DNA molecule encoding a daunorubicin 14-hydroxylase, wherein said DNA molecule has a sequence selected from the group consisting of:
   a) SEQ ID NO: 1,
   b) a DNA sequence encoding the amino acid sequence of SEQ ID NO:2,
   c) a 3.4 kb SphI fragment as shown in FIG. 1, and
   d) an NdeI—BamHI fragment as shown in FIG. 2.

2. The DNA molecule according to claim 1, wherein said DNA molecule is the 3.4 kb SphI fragment of FIG. 1.

3. The DNA molecule according to claim 1, wherein said DNA molecule is the NdeI—BamHI fragment of FIG. 2.

4. The DNA molecule according to claim 1, wherein said DNA molecule encodes a daunorubicin 14-hydroxylase having the sequence of SEQ ID NO: 2.

5. The DNA molecule according to claim 1, wherein said DNA molecule is the sequence of SEQ ID NO: 1.

6. The DNA molecule according to claim 1, where said DNA molecule is at least 1.2 kb in length.

7. The DNA molecule according to claim 6, wherein said DNA molecule is between 1.2–2.4 kb in length.

8. A vector encoding a daunorubicin 14-hydroxylase, wherein said vector comprises a DNA molecule which has a sequence selected from the group consisting of:
   a) SEQ ID NO: 1,
   b) a DNA sequence encoding the amino acid sequence of SEQ ID NO:2,
   c) a 3.4 kb SphI fragment as shown in FIG. 1, and
   d) an NdeI—BamHI fragment as shown in FIG. 2.

9. The vector according to claim 8, wherein said vector contains the 3.4 kb SphI fragment of FIG. 1.

10. The vector according to claim 8, wherein said vector contains the NdeI—BamHI fragment of FIG. 2.

11. The vector according to claim 8, wherein said vector encodes a daunorubicin 14-hydroxylase having the sequence of SEQ ID NO: 2.

12. The vector according to claim 8, comprising a sequence which consists of the sequence of SEQ ID NO: 1.

13. The vector according to claim 8, wherein said vector is a plasmid.

14. The vector according to claim 13, wherein said plasmid is pIS23, pIS62 or pIS70.

15. A host cell transformed or transfected with a vector according to claim 8.

16. A host cell according to claim 15, wherein said host cell is a bacterial cell.

17. A host cell according to claim 16, wherein said bacterial cell is a Streptomyces cell.

18. A method for producing doxorubicin, comprising the steps of:
   culturing a host cell transformed or transfected with a vector encoding a daunorubicin 14-hydroxylase in the presence of daunorubicin under conditions such that the daunorubicin is converted to doxorubicin, to produce a culture, wherein said vector comprises a DNA molecule which has a sequence selected from the group consisting of:
   a) SEQ ID NO: 1,
   b) a DNA sequence encoding the amino acid sequence of SEQ ID NO:2,
   c) a 3.4 kb SphI fragment as shown in FIG. 1, and
   d) an NdeI—BamHI fragment as shown in FIG. 2, and isolating the doxorubicin from the culture.

\* \* \* \* \*

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
        ( A ) LENGTH: 1269 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Streptomyces peucetius ( i x ) FEATURE:
        ( A ) NAME/KEY: CDS
        ( B ) LOCATION:1..1269

( x i ) SEQUENCE DESCRIPTION: SEQ ID NO: 1:

```
GTG AGC GGC GAG GCG CCC CGG GTG GCC GTC GAC CCG TTC GCG TGT CCC      48
Val Ser Gly Glu Ala Pro Arg Val Ala Val Asp Pro Phe Ala Cys Pro
 1               5                  10                  15

ATG ATG ACC ATG CAG CGC AAG CCC GAG GTG CAC GAC GCC TTC CGG GAG      96
Met Met Thr Met Gln Arg Lys Pro Glu Val His Asp Ala Phe Arg Glu
             20                  25                  30

GCG GGC CCG GTC GTC GAG GTG AAC GCC CCC GCG GGC GGA CCC GCC TGG     144
Ala Gly Pro Val Val Glu Val Asn Ala Pro Ala Gly Gly Pro Ala Trp
         35                  40                  45

GTC ATC ACC GAT GAC GCC CTC GCC CGC GAG GTG CTG GCC GAT CCC CGG     192
Val Ile Thr Asp Asp Ala Leu Ala Arg Glu Val Leu Ala Asp Pro Arg
     50                  55                  60

TTC GTG AAG GAC CCC GAC CTC GCC CCC GCC GCC TGG CGG GGG GTG GAC     240
Phe Val Lys Asp Pro Asp Leu Ala Pro Ala Ala Trp Arg Gly Val Asp
 65                  70                  75                  80

GAC GGT CTC GAC ATC CCC GTT CCG GAG CTG CGT CCG TTC ACG CTC ATC     288
Asp Gly Leu Asp Ile Pro Val Pro Glu Leu Arg Pro Phe Thr Leu Ile
                 85                  90                  95

GCC GTG GAC GGC GAG GCC CAC CGG CGC CTG CGC CGC ATC CAC GCA CCT     336
Ala Val Asp Gly Glu Ala His Arg Arg Leu Arg Arg Ile His Ala Pro
             100                 105                 110

GCG TTC AAC CCG CGC CGG CTG GCC GAG CGG ACG GAT CGC ATC GCC GCG     384
Ala Phe Asn Pro Arg Arg Leu Ala Glu Arg Thr Asp Arg Ile Ala Ala
         115                 120                 125

ATC GCC GGC CGG CTG CTC ACC GAA CTC GCC GAC GCC TCC GGC CGG TCG     432
Ile Ala Gly Arg Leu Leu Thr Glu Leu Ala Asp Ala Ser Gly Arg Ser
     130                 135                 140

GGC AAA CCG GCC GAG CTG ATC GGC GGC TTC GCG TAC CAC TTC CCG CTG     480
Gly Lys Pro Ala Glu Leu Ile Gly Gly Phe Ala Tyr His Phe Pro Leu
145                 150                 155                 160

TTG GTC ATC TGC GAG CTG CTC GGT GTG CCG GTC ACC GAT CCG GCG ATG     528
Leu Val Ile Cys Glu Leu Leu Gly Val Pro Val Thr Asp Pro Ala Met
                 165                 170                 175

GCC CGC GAG GCC GTC AGC GTT CTC AAG GCA CTC GGC CTC GGC GGC CCG     576
Ala Arg Glu Ala Val Ser Val Leu Lys Ala Leu Gly Leu Gly Gly Pro
             180                 185                 190

CAG AGC GGC GGG GGT GAC GGC ACG GAC CCT GCC GGG GGC GTG CCG GAC     624
```

-continued

```
            Gln Ser Gly Gly Gly Asp Gly Thr Asp Pro Ala Gly Gly Val Pro Asp
                195                 200                 205

ACC TCG GCC CTG GAG AGC CTG CTC CTC GAA GCC GTG CAC TCA GCC CGG      672
Thr Ser Ala Leu Glu Ser Leu Leu Leu Glu Ala Val His Ser Ala Arg
    210                 215                 220

CGG AAC GAC ACC CCG ACC ATG ACC CGC GTG CTG TAC GAG CGC GCG CAG      720
Arg Asn Asp Thr Pro Thr Met Thr Arg Val Leu Tyr Glu Arg Ala Gln
225                 230                 235                 240

GCC GAG TTC GGC TCG GTC TCC GAC GAC CAG CTC GTC TAC ATG ATC ACC      768
Ala Glu Phe Gly Ser Val Ser Asp Asp Gln Leu Val Tyr Met Ile Thr
                245                 250                 255

GGG CTC ATC TTC GCC GGC CAC GAC ACC ACC GGC TCC TTC CTG GGC TTC      816
Gly Leu Ile Phe Ala Gly His Asp Thr Thr Gly Ser Phe Leu Gly Phe
                260                 265                 270

CTG CTC GCG GAG GTC CTG GCG GGC CGC CTC GCG GCG GAT GCC GAC GAG      864
Leu Leu Ala Glu Val Leu Ala Gly Arg Leu Ala Ala Asp Ala Asp Glu
            275                 280                 285

GAC GCC GTC TCC CGG TTC GTG GAG GAG GCG CTG CGC TAC CAC CCG CCG      912
Asp Ala Val Ser Arg Phe Val Glu Glu Ala Leu Arg Tyr His Pro Pro
        290                 295                 300

GTG CCC TAC ACG TTG TGG AGG TTC GCT GCC ACG GAG GTG ACC ATC GGC      960
Val Pro Tyr Thr Leu Trp Arg Phe Ala Ala Thr Glu Val Thr Ile Gly
305                 310                 315                 320

GGC GTC CGG CTG CCC CGC GGA GCG CCG GTG CTG GTG GAC ATC GAG GGC     1008
Gly Val Arg Leu Pro Arg Gly Ala Pro Val Leu Val Asp Ile Glu Gly
                325                 330                 335

ACC AAC ACC GAC GGC CGC CAT CAC GAC GCC CCG CAC GCC TTC CAC CCG     1056
Thr Asn Thr Asp Gly Arg His His Asp Ala Pro His Ala Phe His Pro
                340                 345                 350

GAC CGT CCC TCG TGG CGG CGG CTC ACC TTC GGC GAC GGG CCG CAC TAC     1104
Asp Arg Pro Ser Trp Arg Arg Leu Thr Phe Gly Asp Gly Pro His Tyr
            355                 360                 365

TGC ATC GGG GAG CAG CTC GCC CAG CTG GAG TCG CGC ACG ATG ATC GGC     1152
Cys Ile Gly Glu Gln Leu Ala Gln Leu Glu Ser Arg Thr Met Ile Gly
        370                 375                 380

GTA CTG CGC AGC AGG TTC CCC GAG GCC CGA CTG GCC GTG CCG TAC GAC     1200
Val Leu Arg Ser Arg Phe Pro Glu Ala Arg Leu Ala Val Pro Tyr Asp
385                 390                 395                 400

GAG TTG CGG TGG TGC CGG AAG GGG GCC CAG ACG GCG CGG CTC ACC GAA     1248
Glu Leu Arg Trp Cys Arg Lys Gly Ala Gln Thr Ala Arg Leu Thr Glu
                405                 410                 415

CTG CCC GTC TGG CTG CGC TGA                                          1269
Leu Pro Val Trp Leu Arg *
                420
```

( 2 ) INFORMATION FOR SEQ ID NO: 2:

( i ) SEQUENCE CHARACTERISTICS:
        ( A ) LENGTH: 422 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 2:

```
Val Ser Gly Glu Ala Pro Arg Val Ala Val Asp Pro Phe Ala Cys Pro
 1               5                  10                  15

Met Met Thr Met Gln Arg Lys Pro Glu Val His Asp Ala Phe Arg Glu
                20                  25                  30

Ala Gly Pro Val Val Glu Val Asn Ala Pro Ala Gly Gly Pro Ala Trp
            35                  40                  45
```

-continued

| | | | | | | | | | | | | | | |
|---|---|---|---|---|---|---|---|---|---|---|---|---|---|---|
| Val | Ile | Thr | Asp | Asp | Ala | Leu | Ala | Arg | Glu | Val | Leu | Ala | Asp | Pro | Arg |
| | 50 | | | | | 55 | | | | 60 | | | | |
| Phe | Val | Lys | Asp | Pro | Asp | Leu | Ala | Pro | Ala | Ala | Trp | Arg | Gly | Val | Asp |
| 65 | | | | | 70 | | | | 75 | | | | | | 80 |
| Asp | Gly | Leu | Asp | Ile | Pro | Val | Pro | Glu | Leu | Arg | Pro | Phe | Thr | Leu | Ile |
| | | | | 85 | | | | | 90 | | | | | 95 | |
| Ala | Val | Asp | Gly | Glu | Ala | His | Arg | Arg | Leu | Arg | Arg | Ile | His | Ala | Pro |
| | | | 100 | | | | | 105 | | | | | 110 | | |
| Ala | Phe | Asn | Pro | Arg | Arg | Leu | Ala | Glu | Arg | Thr | Asp | Arg | Ile | Ala | Ala |
| | | 115 | | | | | 120 | | | | | 125 | | | |
| Ile | Ala | Gly | Arg | Leu | Leu | Thr | Glu | Leu | Ala | Asp | Ala | Ser | Gly | Arg | Ser |
| | 130 | | | | | 135 | | | | | 140 | | | | |
| Gly | Lys | Pro | Ala | Glu | Leu | Ile | Gly | Gly | Phe | Ala | Tyr | His | Phe | Pro | Leu |
| 145 | | | | | 150 | | | | | 155 | | | | | 160 |
| Leu | Val | Ile | Cys | Glu | Leu | Leu | Gly | Val | Pro | Val | Thr | Asp | Pro | Ala | Met |
| | | | | 165 | | | | | 170 | | | | | 175 | |
| Ala | Arg | Glu | Ala | Val | Ser | Val | Leu | Lys | Ala | Leu | Gly | Leu | Gly | Gly | Pro |
| | | | 180 | | | | | 185 | | | | | 190 | | |
| Gln | Ser | Gly | Gly | Gly | Asp | Gly | Thr | Asp | Pro | Ala | Gly | Gly | Val | Pro | Asp |
| | | 195 | | | | | 200 | | | | | 205 | | | |
| Thr | Ser | Ala | Leu | Glu | Ser | Leu | Leu | Leu | Glu | Ala | Val | His | Ser | Ala | Arg |
| | 210 | | | | | 215 | | | | | 220 | | | | |
| Arg | Asn | Asp | Thr | Pro | Thr | Met | Thr | Arg | Val | Leu | Tyr | Glu | Arg | Ala | Gln |
| 225 | | | | | 230 | | | | | 235 | | | | | 240 |
| Ala | Glu | Phe | Gly | Ser | Val | Ser | Asp | Asp | Gln | Leu | Val | Tyr | Met | Ile | Thr |
| | | | | 245 | | | | | 250 | | | | | 255 | |
| Gly | Leu | Ile | Phe | Ala | Gly | His | Asp | Thr | Thr | Gly | Ser | Phe | Leu | Gly | Phe |
| | | | 260 | | | | | 265 | | | | | 270 | | |
| Leu | Leu | Ala | Glu | Val | Leu | Ala | Gly | Arg | Leu | Ala | Ala | Asp | Ala | Asp | Glu |
| | | 275 | | | | | 280 | | | | | 285 | | | |
| Asp | Ala | Val | Ser | Arg | Phe | Val | Glu | Glu | Ala | Leu | Arg | Tyr | His | Pro | Pro |
| | 290 | | | | | 295 | | | | | 300 | | | | |
| Val | Pro | Tyr | Thr | Leu | Trp | Arg | Phe | Ala | Ala | Thr | Glu | Val | Thr | Ile | Gly |
| 305 | | | | | 310 | | | | | 315 | | | | | 320 |
| Gly | Val | Arg | Leu | Pro | Arg | Gly | Ala | Pro | Val | Leu | Val | Asp | Ile | Glu | Gly |
| | | | | 325 | | | | | 330 | | | | | 335 | |
| Thr | Asn | Thr | Asp | Gly | Arg | His | His | Asp | Ala | Pro | His | Ala | Phe | His | Pro |
| | | | 340 | | | | | 345 | | | | | 350 | | |
| Asp | Arg | Pro | Ser | Trp | Arg | Arg | Leu | Thr | Phe | Gly | Asp | Gly | Pro | His | Tyr |
| | | 355 | | | | | 360 | | | | | 365 | | | |
| Cys | Ile | Gly | Glu | Gln | Leu | Ala | Gln | Leu | Glu | Ser | Arg | Thr | Met | Ile | Gly |
| | 370 | | | | | 375 | | | | | 380 | | | | |
| Val | Leu | Arg | Ser | Arg | Phe | Pro | Glu | Ala | Arg | Leu | Ala | Val | Pro | Tyr | Asp |
| 385 | | | | | 390 | | | | | 395 | | | | | 400 |
| Glu | Leu | Arg | Trp | Cys | Arg | Lys | Gly | Ala | Gln | Thr | Ala | Arg | Leu | Thr | Glu |
| | | | | 405 | | | | | 410 | | | | | 415 | |
| Leu | Pro | Val | Trp | Leu | Arg | | | | | | | | | | |
| | | | 420 | | | | | | | | | | | | |

( 2 ) INFORMATION FOR SEQ ID NO: 3:

( i ) SEQUENCE CHARACTERISTICS:
        ( A ) LENGTH: 50 amino acids
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CCCGCGGCGG CGGGCGGTGC CATATGAGCG GCGAAGCGCC GCGTGTGGCC G  51

( 2 ) INFORMATION FOR SEQ ID NO: 4:

( i ) SEQUENCE CHARACTERISTICS:
        ( A ) LENGTH: 58 amino acids
        ( B ) TYPE: nucleic acid
        ( C ) STRANDEDNESS: single
        ( D ) TOPOLOGY: linear ( x i ) SEQUENCE DESCRIPTION: SEQ ID NO: 4:

TCGACGGCCA CACGCGGCGC TTCGCCGCTC ATATGGCACC GCCCGCCGCC GCGGGGTAC  59